United States Patent [19]

Miyazaki et al.

[11] Patent Number: 4,872,758
[45] Date of Patent: Oct. 10, 1989

[54] FILM THICKNESS-MEASURING APPARATUS

[75] Inventors: Takao Miyazaki; Yoshiro Yamada; Isamu Komine, all of Tokyo, Japan

[73] Assignee: NKK Corporation, Tokyo, Japan

[21] Appl. No.: 223,275

[22] Filed: Jul. 22, 1988

[30] Foreign Application Priority Data

Jul. 23, 1987 [JP] Japan .................. 62-184250

[51] Int. Cl.⁴ ............................................. G01B 11/06
[52] U.S. Cl. ................................ 356/381; 356/382; 356/369
[58] Field of Search ................ 356/381, 138, 382, 369

[56] References Cited

U.S. PATENT DOCUMENTS

| 3,985,447 | 10/1976 | Aspnes | 356/369 |
| 4,606,641 | 8/1986 | Yamada et al. | 356/382 |
| 4,623,254 | 11/1986 | Imose | 356/381 |
| 4,695,162 | 9/1987 | Itonaga et al. | 356/138 |

Primary Examiner—Léon Scott, Jr.
Attorney, Agent, or Firm—Frishauf, Holtz, Goodman & Woodward

[57] ABSTRACT

Circularly polarized light caused to be incident on a film surface is converted into three light beams by optical flats to obtain electrical signals corresponding to the intensities of the respective light beams. Two ellipsometric parameters $\psi$ and $\Delta$ are claculated from these three electrical signals.

10 Claims, 7 Drawing Sheets

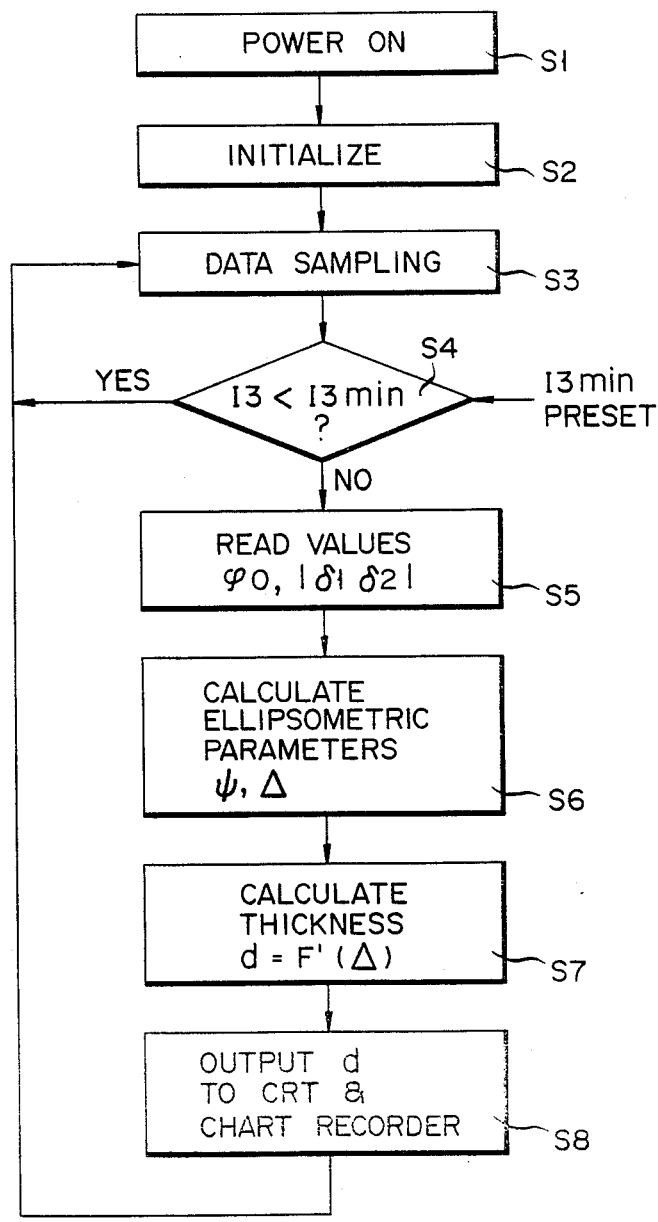
F I G. 3

FILM THICKNESS-MEASURING APPARATUS

BACKGROUND OF THE INVENTION

1. Field of the Invention

The present invention relates to a film thickness-measuring apparatus suitably used for measuring the film thickness of an object to be measured, which is moved at high speed, e.g., the film thickness of an oil coated on a steel plate in a rolling line or a plating line, or the film thicknesses of other thin films, in an on-line manner.

2. Description of the Related Art

Ellipsometry is generally used as a means for measuring the film thickness of a thin film having a film thickness of several 1,000 Å. According to this method, a change in polarization state when light is reflected by a thin film sample surface, i.e., ratio $\rho$ of Fresnel complex amplitude reflection coefficient rp of one electrical vector component (p component) parallel to an incidence plane to Fresnel complex amplitude reflection coefficient rs of the other component (s component) perpendicular to the incidence plane is obtained by equation (1) below, and film thickness d is obtained in accordance with a predetermined function of already established reflection coefficient ratio $\rho$ and film thickness d.

$$\rho = rp/rs = \tan \psi e^{j\Delta} \quad (1)$$

Since reflection coefficient ratio $\rho$ is a complex number, two ellipsometric parameters, i.e., amplitude ratio $\tan \psi$ and phase $\Delta$ must be obtained. One of conventional means for obtaining these two ellipsometric parameters $\psi$ and $\Delta$ at high speed is disclosed in U.S. patent application Ser. No. 62,242.

According to this means, linearly polarized light formed by a polarizer and having a predetermined azimuth is caused to be incident on the incidence surface of an object to be measured at a predetermined angle. Then, the light reflected by the object is converted into a plurality of light beams using a beam splitter section. The plurality of light beams are caused to pass through a plurality of analyzers having different transmission polarization azimuths, and are respectively focused by a plurality of focusing lenses at predetermined focal lengths. The plurality of light beams focused by these focusing lenses are detected by a plurality of photodetectors through pinholes located at the respective focal points, thereby outputting electrical signals corresponding to the respective light amounts/intensities. Then, the respective electrical signals from these photodetectors are subjected to a predetermined arithmetic operation so as to obtain two ellipsometric parameters, i.e., amplitude ratio $\tan \psi$ and phase $\Delta$. With this operation, two ellipsometric parameters $\psi$ and $\Delta$ can be reliably obtained using a fixed optical system. The film thickness or refractive index of the object to be measured can be calculated on the basis of these parameters.

As described above, the method disclosed in U.S. patent application Ser. No. 62,242 exhibits excellent characteristics compared with other conventional methods. However, when the film thickness of a transparent film formed on a transparent glass substrate is measured, the following problems are posed. In the invention disclosed in Ser. No. 62,242, linearly polarized light is used as incident light, reflected light is branched into three beams by a beam splitter constituted by three or more parallel flat optical flats, analyzers having predetermined transmission axis angles with respect to the branch beams are arranged, and the light amounts of the three branch beams after passing through the analyzers are measured. In this case, as is apparent from the description of the embodiment of this application, ellipsometric parameter $\Delta$ is obtained from the intensities of the three light beams I1, I2, and I3 as phase cosine $\cos \Delta$. In this case, if a polarizer azimuth is set to be 45°, analyzer azimuth $\alpha 1 = 0°, \alpha 2 = 45°$, and $\alpha 3 = -45°$, then $$\cos(\Delta - \phi 0) = \{(I2 - I3)/2I1\} \sqrt{I1/(I2 + I3 - I1)} \quad (2)$$

$$\tan \psi = |\sigma 1 \sigma 2| \sqrt{I1/(I2 + I3 - I1)} \quad (3)$$

When the optical flats are transparent, $\phi 0 = 0°$. Thus, $\cos (\Delta - \phi 0) = \cos \Delta$ according to equation (2). Furthermore, ellipsometric parameter $\Delta$ may become close to 180° when, e.g., the film thickness of a transparent film formed on a transparent glass substrate or the like is measured. In such a case, since the rate of change in $\cos \Delta$ is close to 0 when $\Delta$ is close to 0° or 180°, even if a small error is included in the right side of equation (2), an error in $\Delta$ becomes large, and hence accurate measurement cannot be performed.

SUMMARY OF THE INVENTION

It is an object of the present invention to provide a film thickness-measuring apparatus capable of accurately measuring the film thickness of a transparent film formed on a transparent glass substrate even if the phase of the ellipsometric parameter is close to 0° to 180°.

According to the present invention, circularly polarized light formed by a polarizer and a $\lambda/4$ plate is caused to be incident on an incidence plane of an object to be measured at a predetermined angle, the light reflected by the object is converted into a plurality of light beams using a beam splitter section, the plurality of light beams are caused to pass through a plurality of analyzers having different transmission polarization azimuths, the light beams are respectively focused by a plurality of focusing lenses at predetermined focal lengths, the plurality of light beams focused by the focusing lenses are detected by a plurality of photodetectors located at the respective focal points to output electrial signals corresponding to the respective amounts/intensities, and the respective electrical signals from the photodetectors are supplied to an arithmetic processing section and are subjected to a predetermined arithmetic operation, thereby obtaining two ellipsometric parameters, i.e., an amplitude ratio and a phase.

According to the above-described method, since film thickness measurement is performed using circularly polarized light as incident light, an equation corresponding to equation (2) is given by:

$$\sin(\Delta - \phi 0) = \{(I2 - I3)/2I1\} \sqrt{I1/(I2 - I3 - I1)} \quad (4)$$

In this case, since the rate of change in $\sin \Delta$ becomes maximum when phase $\Delta$ is close to 0° or 180°, $\Delta$ can be obtained with high precision even if phase $\Delta$ is close to 0° or 180°, and hence film thickness measurement can be performed with high precision.

BRIEF DESCRIPTION OF THE DRAWINGS

FIG. 3 is a flow chart of an operation of a microcomputer in the embodiment;

DETAILED DESCRIPTION OF THE PREFERRED EMBODIMENTS

Embodiments of the present invention will be described in detail with reference to the accompanying drawings.

Figure 1:
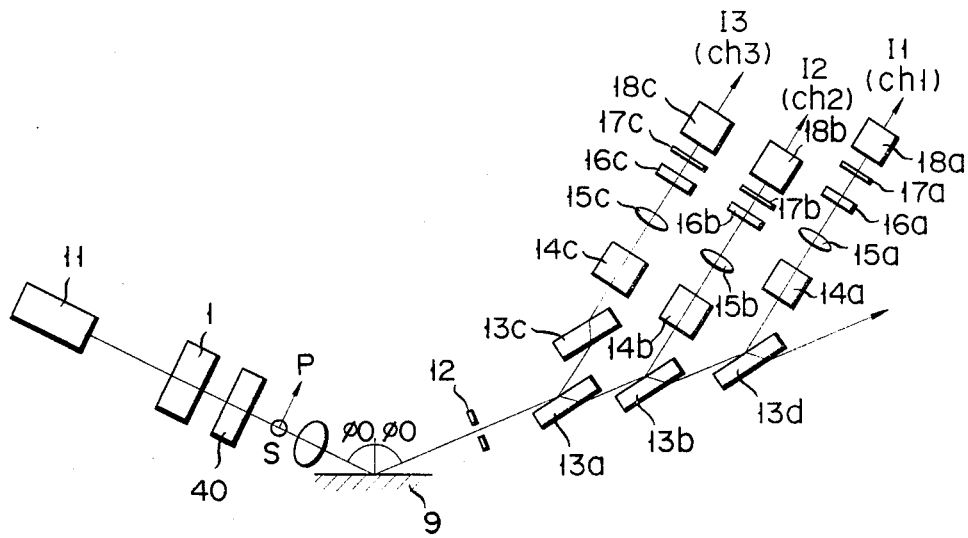
FIG. 1 is a view illustrating part of an optical system of an apparatus according to an embodiment of the present invention.

Referring to FIG. 1, reference numeral 11 denotes a collimated monochromatic light source. Light emitted from light source 11 is formed into a linearly polarized light having predetermined azimuth $\theta$ by polarizer 1, converted into circularly polarized light through $\lambda/4$ plate 40, and is incident on sample surface 9 at predetermined angle $\phi 0$. Note that the incidence plane of sample surface 9 is parallel to the surface of the drawing and the light propagation direction is the Z direction. In addition, a coordinate axis forming 90° with the light propagation direction Z is defined as the P axis, and a coordinate axis perpendicular to the P and Z directions is defined as the S axis, so that the P, S, and Z directions constitute a right-handed orthogonal coordinate system on the incidence plane. All the polarizer and analyzer angles are set such that the P axis is 0° and the S axis is 90°.

The light reflected (reflection angle $\phi 0$) by sample surface 9 is branched into three light beams by four optical flats (beam splitter sections) 13a, 13b, 13c, and 13d of an identical material and shape through aperture 12 for limiting beam size. Optical flats 13a to 13d are optically isotropic and transparent, and are fixed parallel to each other. The thicknesses and intervals of optical flats 13a to 13d are set such that multiple-reflected light is not detected.

Of the three light beams, a light beam transmitted through two optical flats 13a and 13b and reflected by optical flat 13d is set for channel ch1, a light beam transmitted through optical flat 13a and reflected by optical flat 13b is set for channel ch2, and a light beam transmitted through optical flat 13a and reflected by optical flat 13c is set for channel ch3. The light beams for channels ch1 to ch3 become parallel to each other. Then, the light beams pass through analyzers 14a to 14c having fixed transmission azimuths $\alpha 1$ to $\alpha 3$, and focused by condenser lenses 15a to 15c having the same focal length. The focused light beams pass through pinholes 16a to 16c. After external disturbing light is removed by interference filters 17a to 17c, the resultant light beams are supplied to photodetectors 18a to 18c to be converted into electrical signals I1 to I3 corresponding to the respective light intensities. Subsequently, electrical signals I1 to I3 are subjected to a predetermined arithmetic operation in the signal processing circuit shown in FIG. 2, thereby calculating ellipsometric parameters $\phi$ and $\Delta$.

Figure 2:
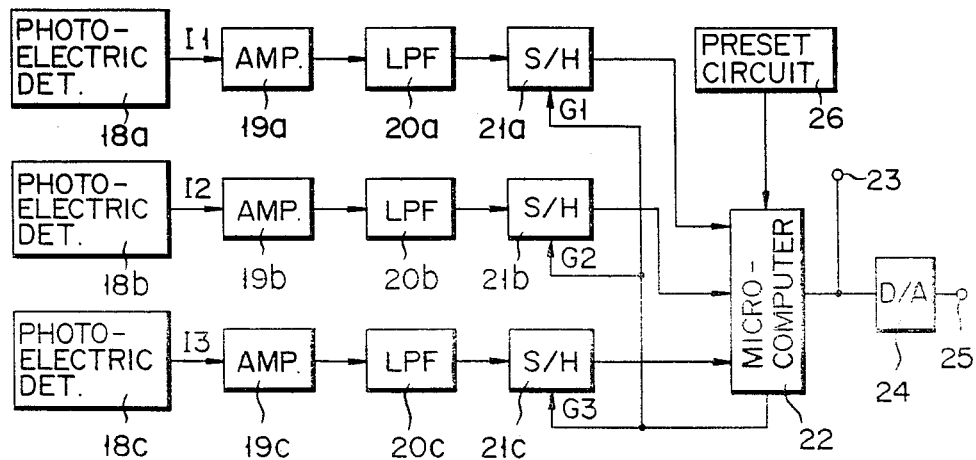
FIG. 2 is a block diagram showing part of a signal processing system of the apparatus according to the embodiment.

Referring to FIG. 2, electrical signals I1 to I3 for channels ch1, ch2, and ch3 respectively output from photodetectors 18a to 18c are amplified by amplifiers 19a to 19c. After noise components of electrical signals I1 to I3 are removed by low-pass filters 20a to 20c, electrical signals I1 to I3 are supplied to sample and hold circuits (to be referred to as S/H circuits hereinafter) 21a to 21c. S/H circuits 21a to 21c simultaneously sample and hold the respective output signals of channels ch1, ch2, and ch3 using gate signal G output from microcomputer 22. The respective output signals from channels ch1 to ch3 simultaneously sampled, i.e., electrical signals I1 to I3, are supplied to microcomputer 22. Then, microcomputer 22 performs the following arithmetic processing so that ellipsometric parameters $\psi$ and $\Delta$ are output from output terminal 23 as digital information. In addition, the digital information is output from output terminal 25 as analog information through D/A converter 24. Note that reference numeral 26 denotes a preset circuit for presetting each channel gain, specific values $\phi 0 | \sigma 1 \sigma 2 |$ and minimum light amount level I3min.

In microcomputer 22, outputs I1 to I3 of channels ch1 to ch3 are calculated using the Jones matrix method. More specifically, first ellipsometric parameters $\psi$ and $\Delta$ of an object to be measured are defined by equation (5) as follows:

$$\mathrm{rp/rs} = \tan \psi e^{j\Delta} \qquad (5)$$

where rp is the amplitude reflectivity of the P polarization electrical vector (in the incidence plane) in the object to be measured, and rs is the amplitude reflectivity of the S polarization electrical vector (in direction perpendicular to the incidence plane) in the object.

In addition, amplitude transmittance ratio $\sigma 1$ and amplitude reflectivity ration $\sigma 2$ between the P and S polarization electrical vectors of optical flats 13a to 13d are defined by equations (6) and (7):

$$\sigma 1 = \mathrm{ts'/tp'} = |\sigma 1| e^{j\phi 1} \qquad (6)$$

$$\sigma 2 = \mathrm{rs'/rp'} = |\sigma 2| e^{j\phi 2} \qquad (7)$$

where $$\phi 0 = \phi 1 + \phi 2 \qquad (8)$$

In equations (6) to (8), tp' and ts' are the P and S Fresnel complex amplitude transmission coefficients of optical flats 13a to 13d, rp' and rs' are the P and S Fresnel complex amplitude reflection coefficients of optical flats 13a to 13d, $\phi 1$ and $\phi 2$ are the phases of $\sigma 1$ and $\sigma 2$, and $\phi 0$ is the sum of the phases of $\sigma 1$ and $\sigma 2$.

According to the above definitions, light intensity outputs I1 to I3 of channels ch1 to ch3 can be represented by:

$$I1 = K1\tau 1|rs|^2|tp'|^4|rp'|^2 I0\{\tan^2\psi\cos^2\alpha 1 \pm \quad (9)$$
$$2\tan\psi|\sigma 1^2\sigma 2^2|\sin\alpha 1\cos\alpha 1\sin(\Delta - 2\phi 1 - \phi 2) +$$
$$|\sigma 1^2\sigma 2|^2\sin^2\alpha 1\}$$

where signs "+" and "−" denote right- and left-circularly polarized light, respectively.

$$I2 = K2\tau 2|rs|^2|tp'|^2|rp'|^2 I0\{\tan^2\psi\cos^2\alpha 2 \pm \quad (10)$$
$$2\tan\psi|\sigma 1\sigma 2|\sin\alpha 2\cos\alpha 2\sin(\Delta - \phi 0) +$$
$$|\sigma 1\sigma 2|^2\sin^2\alpha 2\}$$

where signs + and − have the same meanings as in equation (9).

$$I3 = K3\tau 3|rs|^2|tp'|^2|rp'|^2 I0\{\tan^2\psi\cos^2\alpha 3 \pm \quad (11)$$
$$2\tan\psi|\sigma 1\sigma 2|\sin\alpha 3\cos\alpha 3\sin(\Delta - \phi 0) +$$
$$|\sigma 1\sigma 2|^2\sin^2\alpha 3\}$$

where signs + and − have the same meanings as in equation (9). In equations (9) to (11), K1 to K3 are the detector gains of channels ch1 to ch3, $\tau 1$ to $\tau 3$ are the transmittances of analyzers 14a to 14c and photodetectors 18a to 18c of channels ch1 to ch3, I0 is the intensity of incident light, and $\alpha 1$ to $\alpha 3$ are the azimuths of photodetectors 14a to 14c of channels ch1 to ch3.

In this case, detector gains K1 to K3 of channels ch1 to ch3 are adjusted such that each of outputs I1 to I3 becomes predetermined value $I_G \tan^2\psi$ with respect to arbitrary reflected light ($\psi$, $\Delta$) when all photodetector azimuths $\alpha 1$ to $\alpha 3$ of channels ch1 to ch3 are set to be 0°. Since $$K1\tau 1|rs|^2|tp'|^4|rp'|^2 I0\tan^2\psi = \quad (12)$$
$$K2\tau 2|rs|^2|tp'|^2|rp'|^2 I0\tan^2\psi = K3\tau 3|rs|^2|tp'|^2|rp'|^2 I0\tan^2\psi =$$
$$I_G\tan^2\psi$$

equations (9) to (11) are rewritten using equation (12) as follows:

$$I1 = I_G\{\tan^2\psi \cos^2\alpha 1 \pm 2\tan\psi|\sigma 1\sigma 2|\sin\alpha 1\cos\alpha 1$$
$$\sin(\Delta - 2\phi 1 - \phi 2) + |\sigma 1\sigma 2|^2\sin^2\alpha 1\} \quad (9')$$

$$I2 = I_G\{\tan^2\psi \cos^2\alpha 2 \pm 2\tan\psi|\sigma 1\sigma 2|\sin\alpha 2\cos\alpha 2$$
$$\sin(\Delta - \phi 0) + |\sigma 1\sigma 2|^2\sin^2\alpha 2\} \quad (10')$$

$$I3 = I_G\{\tan^2\psi \cos^2\alpha 3 \pm 2\tan\psi|\sigma 1\sigma 2|\sin\alpha 3\cos\alpha 3$$
$$\sin(\Delta - \phi 0) + |\sigma 1\sigma 2|^2\sin^2\alpha 3\} \quad (11')$$

when $\alpha 1 = 0°$, $\alpha 2 = 45°$, and $\alpha = -45°$, outputs I1 to I3 of channels ch1 to ch3 are given by (assuming that right-circulaly polarized light is used):

$$I1 = \tfrac{1}{2} I_G \tan^2\psi \quad (13)$$

$$I2 = \tfrac{1}{2} I_G\{\tan^2\psi + 2\tan\psi|\sigma 1\sigma 2|\times\sin(\Delta - \phi 0) + |\sigma 1\sigma 2|^2\} \quad (14)$$

$$I3 = \tfrac{1}{2} I_G\{\tan^2\psi + 2\tan\psi|\sigma 1\sigma 2|\times\sin(\Delta - \phi 0) + |\sigma 1\sigma 2|^2\} \quad (15)$$

Therefore, according to equations (13) to (15)

$$\sin(\Delta - \phi 0) = \{(I2 - I3)/2I1\}\sqrt{I1/(I2 + I3 - I1)} \quad (16)$$

$$\tan\psi = |\sigma 1\sigma 2|\sqrt{I1/(I2 + I3 - I1)} \quad (17)$$

where $\phi 0$ and $|\sigma 1\sigma 2|$ are the specific values determined by optical flats 13a to 13d.

When an object to be measured is known glass or the like which is transparent and has refractive index n, the eigenvalues can be obtained from outputs I1, I2, and I3 as follows:

$$\phi 0 = -\arcsin[\{(I2 - I3)/2I1\}\sqrt{I1/(I2 + I3 - I1)}\,] \quad (18)$$

$$|\sigma 1\sigma 2| = \{(\sin^2\phi 0 - \cos\phi 0 \sqrt{n^2 - \sin^2\phi 0})/(\sin^2\phi 0 + \quad (19)$$
$$\cos\phi 0 \sqrt{n^2 - \sin^2 0})\}\sqrt{(I2 + I3 - I1)/I1}$$

In equations (18) and (19), $\phi 0$ is an incident angle.

Therefore, two ellipsometric parameters $\phi$ and $\Delta$ can be simultaneously obtained by correcting $\phi 0$ and $|\sigma 1\sigma 2|$ according to equations (16) and (17). In practice, $\phi 0$ is close to 0°, and $|\sigma 1\sigma 2|$ is changed depending on the incident angle of reflected light onto the beam splitter. The value of $|\sigma 1\sigma 2|$ becomes close to 2 when the incident angle is 70°.

As is apparent from equations (16) and (17), since sin $(\Delta - \phi 0)$ and $\tan\psi$ are obtained using outputs I1 to I3 as dimensionless values, and outputs I1 to I3 are simultaneously obtained, these values are completely free from the influences of changes in light amount due to a light source or an object to be measured.

In addition to the above-described conditions, i.e., $\alpha 1 = 0°$, $\alpha 2 = 45°$, $\alpha 3 = -45°$, if $\alpha 1 = 0$ and $\alpha 2 = -\alpha 3$ ($\alpha 2 \neq 0$, 90°), $\psi$ and $\Delta$ can be obtained in the same manner as described above. In this case, equations (16) and (17) are modified as follows:

$$\sin(\Delta - \phi 0) = \{(I2 - I3)/2\sqrt{2}\,\cos\alpha 2 I1\}\cdot \quad (20)$$
$$\sqrt{I1/(I2 + I3 - 2\cos^2\alpha 2 I1)}$$

$$\tan\psi = \sqrt{2}\,|\sigma 1\sigma 2|\sin\alpha 2 \sqrt{I1/(I2 + I3 - 2\cos^2\alpha 2 I1)} \quad (21)$$

In the apparatus of the present invention, in order to eliminate a measurement error due to a tilt of an object to be measured, pinholes 16a to 16c are arranged in front of photodetectors 18a to 18c so as to narrow the measurement visual field angle. More specifically, when the object is tilted and incident angle $\phi 0$ is changed by $\pm 1.0°$, a measurement error of a film thickness reaches several 10 Å. For this reason, in the apparatus of the present invention, the measurement visual field is narrowed to $\pm 0.2°$ or less. Assuming that the focal lengths of focusing lenses 15a to 15c are f and the diameters of the pinholes are D, then the measurement visual field is determined by the following condition:

$$D \leq 0.7 \times 10^{-3} f \quad (22)$$

With this operation, when the object is tilted by 0.2° or more, reflected light is shielded by pinholes 16a to 16c, and hence the light amount level is dropped. Therefore, when one of photoelectric outputs I1 to I3 of the three channels, e.g., I3 is monitored, and then, lowermost limit level I3min is set and a condition of I3 < I3min is satisfied, monitored I3 is not used as a measurement value. By performing such a countermeasure and keeping the stability of each of photodetectors 18a to 18c to be 1% or less, a measurement precision of ±5 Å can be obtained.

FIG. 3 is a flow chart for explaining an operation of microcomputer 22 in FIG. 2. Referring to FIG. 3, when the power is turned on in step S1, monochromatic light source 11 in FIG. 1 is turned on, and all the circuit elements in FIG. 2 are energized. In step S2, the contents of microcomputer 22 are initialized, and S/H circuits 21a to 21c are cleared by gate outputs G1 to G3 from microcomputer 22. At the same time, the values of each channel gain, $\phi 0$, $|\sigma 1, \sigma 2|$, and I3min are output, thereby performing a preset operation.

Upon completion of the initialization, the flow advances to next step S3, and output data I1 to I3 from the respective channels are sampled by S/H circuits 21a to 21c using sampling signal G from microcomputer 22. When the data sampling in step S3 is completed, the flow advances to next step S4, and minimum value I3min preset by preset circuit 26 is compared with output data I3 held by S/H circuit circuit 21c. If I3 < I3min, it is determined that I3 is not suitable for correct measurement of a film thickness, so that the flow returns to step S3 to perform data sampling again. If I3 ≧ I3min in step S4, I3 is determined to be valid data, so that data I1 to I3 held in S/H circuits 21a to 21c are supplied to microcomputer 22. In this case, data I1 to I3 can be represented by equations (13) to (15), as described above. Therefore, arithmetic operations of equations (16) and (17) are performed according to a program set in microcomputer 22 in advance.

More specifically, in step S5, the fixed value of phase difference $\psi 0$ determined by optical flats 13a to 13d, and the absolute value of $|\sigma 1\sigma 2|$ are read out from a predetermined memory in microcomputer 22. Then, in next step S6, arithmetic operations of equations (16) and (17) are performed using the readout values of $\phi 0$ and $|\sigma 1\sigma 2|$, and obtained data I1 to I3. Ellipsometric parameters $\psi$ and $\Delta$ are obtained on the basis of these arithmetic operations. In the next step S7, an operation of $d = K\Delta$ is performed using ellipsometric parameter $\Delta$ obtained in this manner, thereby obtaining film thickness d on sample surface 9. The data of obtained film thickness d is converted into an analog value by D/A converter 24. Then, the analog value is output to a CRT or a chart printer (not shown) in the next step S8, and the flow returns to step S3.

As described above, according to the present invention, both two ellipsometric parameters $\psi$ and $\Delta$ can be obtained at the light speed if response time of photodetectors 18a to 18c is not considered. With this operation, even if an object to be measured is moved at a high speed of 5 m/sec or more, a time delay is not caused, and hence film thickness at a given point or complex index of refraction can be accurately obtained.

In addition, according to the present invention, since all the optical system components associated with the fundamental measuring operation are fixed, a mechanical movable section and a magnetic electric polarizer such as a Faraday element or a KDP element are not required. Accordingly, the structure of the present invention is simple and strong, and moreover, free from the influences of an error due to changes in temperature and the like. Since a measurement amount is converted into a dimensionless value, it is totally free from the influences of changes in light amount. Moreover, since the field of vision of each light-receiving unit (photodetectors 18a to 18c) is narrowed to 0.2° or less, the influences of changes in angle of an object to be measured can be minimized.

Figure 4:
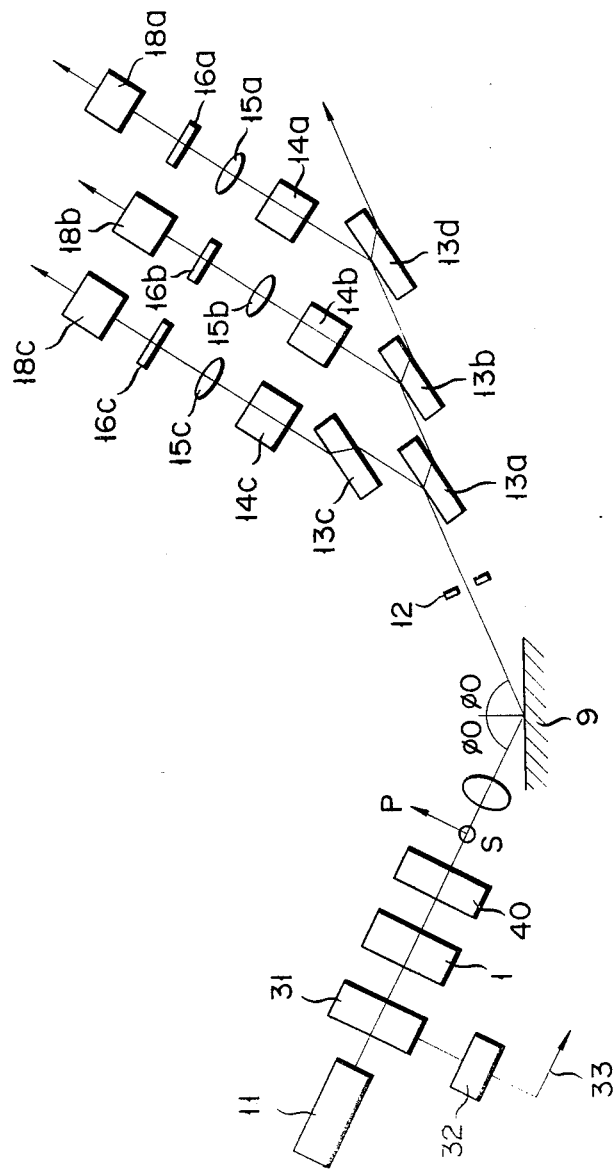
FIG. 4 is a view illustrating an optical system of an apparatus according to another embodiment.
Figure 5:
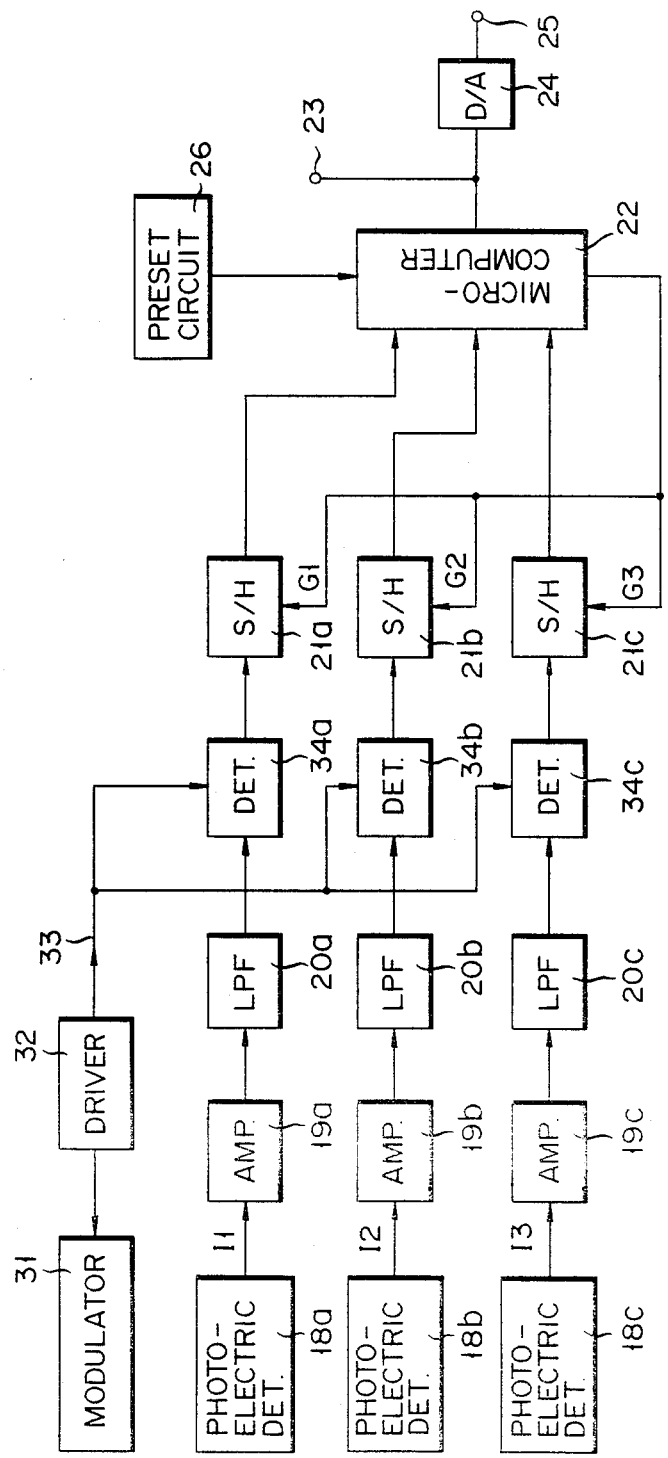
FIG. 5 is a block diagram showing a signal processing system of the apparatus according to another embodiment.

Note that the present invention is not limited to the above-described embodiment. For example, unlike the above embodiment wherein external disturbing light is removed by interference filters 17a to 17c, modulator 31 such as an ultrasonic modulator or a chopper may be arranged between light source 11 and polarizer 1, and modulator 31 is driven by modulator driver 32 so that external disturbing light can be removed by modulating incident light without using interference filters 17a to 17c, as shown in FIG. 4. In this case, however, in a signal processing system, the outputs from channels ch1 to ch3 must be synchronously detected by supplying modulation reference signals output from modulator driver 32 to synchronous detectors 34a to 34c, as shown in FIG. 4.

In the above embodiment, the normal of optical flats 13a to 13d are present within the incidence plane. However, even when the normal is set to be perpendicular to the incidence plane, measurement can be performed in the same manner as in the above embodiment. In this case, reflected light is reflected by optical flats 13a to 13d in the horizontal direction (perpendicular to the surface of the drawing), and hence the plane of polarization is rotated 90°. Therefore, equations (16) and (17) are transformed into the following equations (23) and (24):

$$\sin(\Delta + \phi 0) = \{(I3 - I2)/2I1\} \sqrt{I1/(I2 + I3 - I1)} \quad (23)$$

$$\tan\psi = \{1/|\sigma 1\sigma 2|\} \sqrt{(I2 + I3 - I1)/I1} \quad (24)$$

Although in the above-described embodiment, an object moving at high speed is exemplified as an object to be measured, a stationary object may be the one to be measured. In the industrial fields of semiconductors and electronics, the present invention can be applied as a film thickness-measuring apparatus which is lower in cost and higher in speed than the conventional apparatuses. Various changes and modifications can be made without departing from the scope and spirit of the present invention.

As has been described above in detail, according to the present invention, since circularly polarized light is used as incident light, there is provided a film thickness-measuring apparatus which can measure the film thickness of a transparent film formed on a transparent glass substrate with high precision.

In addition, the apparatus of the present invention can be realized by changing a calculation method using a simple arrangement wherein a $\lambda/4$ plate is added to the apparatus of the previous invention. When the slow axis or fast axis of the $\lambda/4$ plate is matched with the transmission axis of the polarizer, light transmitted through the $\lambda/4$ plate remains linearly polarized light. When the slow axes of the $\lambda/4$ plate and the polarizer are tilted by 45°, light transmitted through the $\lambda/4$ plate becomes circularly polarized light. Since this is a known technique, by employing the arrangement of the present invention, the techniques disclosed in the previous and present inventions can be easily selected and practiced by only properly setting the angle of the λ/4 plate and selecting calculation formula.

Figure 6:
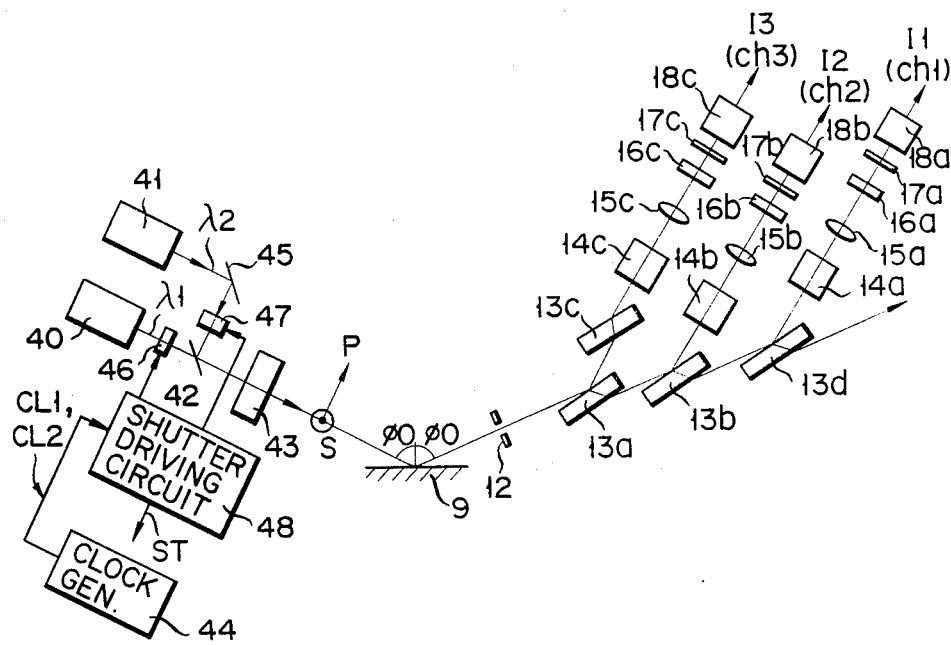
FIG. 6 is a block diagram showing the optical system used in a third embodiment of the invention.
Figure 7:
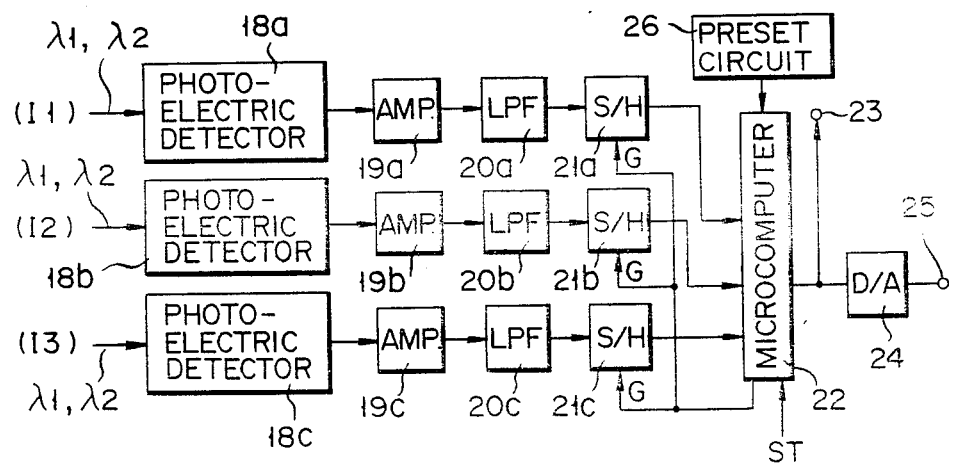
FIG. 7 is a block diagram illustrating the electric circuit used in the third embodiment.

FIGS. 6 and 7 show a third Embodiment of the invention, which can obtain correct ellipsometric parameters ψ and Δ, and can thus accurately measure thickness of an oil film even if the refractive index or the surface roughness of steel plate 9 changes while plate 9 is moving. The third embodiment has means for applying to oil surface on sample 9 two linearly polarized light beams having different wavelengths. It also has means for receiving the light beams reflected from sample steel plate 9 with oil film coated, and calculating the thickness of oil film from the relationship between the phase-cosine of the light reflected from stel plate 9 with oil film coated, for the 2 light beams with different wavelengths. The relationship, from which the thickness of coated film is obtained, is the difference between these phase-cosine values, for example.

Before describing the structure of the apparatus shown in FIGS. 6 and 7, the experiment conducted by the inventors hereof to invent this third embodiment will be explained.

(1) Two light beams having different wavelengths $\lambda_1$ and $\lambda_2$ were polarized into circularly polarized light beams. The polarized light beams were applied to a tin-plated steel plate at the same incidence angle. The light beam reflected from the surface of the steel plate had each an elliptical cross section. Phase cosines cos $\Delta\lambda_{1,s}$ and cos $\Delta\lambda_{2,s}$ of the reflected light beams changed in proportion to the slight change in the surface roughness or refractive index of the steel plate. That is:

$$\cos \Delta\lambda_{2,s} = l \cos \Delta\lambda_{1,s} - m \quad (25)$$

where l and m are constants determined by wavelengths $\lambda_1$ and $\lambda_2$. In this experiment, wavelengths $\lambda_1$ and $\lambda_2$ were 633 nm and 514 nm, respectively. Phase-cosine cos $\Delta\lambda_{1,s}$ for the light ray having wavelength $\lambda_1$ and phase-cosine cos $\Delta\lambda_{2,s}$ for the light ray having wavelength $\lambda_2$ changed in proportion to each other, as the surface roughness or refractive index of the steel plate varied slightly.

(2) As far as a transparent film having thickness of hundreds of angstroms or less and coated on a flat object was concerned, the difference between the phase-cosine of the light beam having wavelength $\lambda_1$ and reflected from the film on the substrate and the phase-cosine of the light beam having the same wavelength and reflected from the of the substrate without film was proportionate to the thickness d of the film. The same held true in the case of the light beam having wavelength $\lambda_2$. Namely:

$$d = k_1(\cos \Delta\lambda_1 - \cos \Delta\lambda_{1,s}) \quad (26)$$

$$d = k_2(\cos \Delta\lambda_2 - \cos \Delta\lambda_{2,s}) \quad (27)$$

where $k_1$ is the proportional coefficient for wavelength $\lambda_1$, and $k_2$ is the proportional coefficient for wavelength $\lambda_2$. These coefficients $k_1$ and $k_2$ are constants determined by the incidence angle $\phi_0$ of the circularly polarized light beam applied to the transparent film and by the properties of the film whose thickness d will be measured. More precisely, coefficients $k_1$ and $k_2$ can be regarded as being constant, provided that the complex refractive index $N_2$ of the substrate changes by ±10% or less as is represented by the following relation:

$$|N2 - N2| \leq 0.1|N2| \quad (28)$$

The difference between the phase-cosine of the light reflected from the thin film on the substrate and the phase-cosine of the light reflected from the substrate without film is proportionate to the thickness d of the film. It follows that thickness d can be accurately measured from equations (25), (26) and (27), even if the refractive index or the surface roughness of the substrate changes. That is:

$$d = \frac{k_1 k_2}{k_1 - k_2 l}(\cos\Delta\lambda_2 - l\cos\Delta\lambda_1 + m) \quad (29)$$
$$= A\cos\Delta\lambda_2 + B\cos\Delta\lambda_1 + C$$

where A, B and C are constants which can be experimentally determined once incidence angle $\phi_0$ has been set.

The structure of the apparatus shown in FIGS. 6 and 7, which is the third embodiment of the invention, will now be described. FIG. 6 schematically illustrates the optical system of the third embodiment. The optical system includes two light sources 40 and 41. Light source 40 emits a collimated monochromatic ray having wavelength $\lambda_1$, and light source 41 emits a collimated ray having wavelength $\lambda_2$. The ray emitted from light source 40 passes semi-transparent mirror 42 an polarized by polarizer 43 into a circularly polarized ray. This polarized ray is applied to the surface of object 9 at incidence angle of $\phi_0$. The ray emitted from light source 41 is reflected by reflector 45 and also by semi-transparent mirror 42, and then polarized by polarizer 43 into a circularly polarized ray. This ray is also applied to object 9 at the same incidence angle of $\phi_0$. Shutter 46 is provided between light source 40 and semitransparent mirror 42, and shutter 47 is provided between light source 41 and semi-transparent mirror 42. These shutters 46 and 47 are driven by shutter-driving circuit 48, and thus are opened and closed. Shutter-driving circuit 28 generates shutter drive signals ST, which are supplied to microcomputer 22.

The light-receiving section of the optical system shown in FIG. 6 is identical to that of the optical system shown in FIG. 1. The same components as those of the section shown in FIG. 1 are designated by the same numerals in FIG. 6, and will not be described in detail.

FIG. 7 shows the signal-processing section of the second embodiment. This section is also identical to the signal-processing section of the first embodiment. Microcomputer 22 receives the output signals of S/H circuits 21a, 21b and 21c in response to shutter drive signals ST supplied from shutter-driving circuit 48. Microcomputer 22 processes these signals, thereby obtaining phase-cosine cos $\Delta\lambda_1$ for the circularly polarized ray having wavelength $\lambda_1$ and also phase-cosine cos $\Delta\lambda_2$ for the circularly polarized ray having wavelength $\lambda_2$, and then calculate thickness d from the phase cosines thus obtained. The digital data showing thickness d is output via output terminal 23, and also input to D/A converter 24. D/A converter 24 converts the digital data to analog data. The analog data is input from terminal 25 to a chart recorder (not shown).

The operation of the third embodiment will now be explained. Shutter-driving circuit 48 opens one of two shutters 46 and 47, while closing the other of these shutters 46 and 47. More specifically, clock generator 44 generates two clock signals CL1 and CL2 which are 180° out of phase with each other. Here, two acoustic optical modulator are used as two optical shutters. Clock signals CL1 and CL2 are supplied to shutter-driving circuit 48. Circuit 48 supplies clock signal CL1 to shutter 46, and clock signal CL2 to shutter 47, whereby shtters 46 and 47 are alternately opened and closed. When shutter 46 is opened by clock signal CL1, the Helium-Neon laser beam of wavelength $\lambda_1$ emitted from light source 40 is applied to object 9 via semitransparent mirror 42 and polarizer 43, reflected from object 9, and split into three beams by optical flats 13a, 13b, 13c and 13d. These beams are applied to photoelectric detectors 18a, 18b and 18c. When shutter 47 is opened by clock signal CL2, the Argon laser beam of wavelength $\lambda_2$ emitted from light source 41 is applied to object 9 after it has been reflected by semi-transparent mirror 42 and passed through polarizer 43. The polarized Argon laser beam is reflected from object 9 and split into three beams by optical flats 13a, 13b, 13c and 13d. The three beams are applied to photoelectric detectors 18a, 18b and 18c.

Photoelectric detectors 18a, 18b and 18c generate electric signals representing $(I_1)\lambda_1,\lambda_2$ $(I_2)\lambda_1,\lambda_2$ and $(I_3)\lambda_1,\lambda_2$. The electric signals are amplified by amplifiers 19a, 19b and 19c, sampled and held by S/H circuits 21a, 21b and 21c, and finally input to microcomputer 22. Micro-computer 22 processes these input signals, thereby calculating phase-cosine $\Delta\lambda_1$ and $\Delta\lambda_2$ for wavelengths $\lambda_1$ and $\lambda_2$, as follows:

$$\sin(\Delta\lambda_1 - \phi_{0\lambda_1}) = \tag{37}$$

$$\frac{(I_2)\lambda_1 - (I_3)\lambda_1}{2(I_1)\lambda_1} \sqrt{\frac{(I_1)\lambda_1}{(I_2)\lambda_1 + (I_3)\lambda_1 - (I_1)\lambda_1}}$$

$$\sin(\Delta\lambda_2 - \phi_{0\lambda_2}) = \tag{38}$$

$$\frac{(I_2)\lambda_2 - (I_3)\lambda_2}{2(I_1)\lambda_2} \sqrt{\frac{(I_1)\lambda_2}{(I_2)\lambda_2 + (I_3)\lambda_2 - (I_1)\lambda_2}}$$

The following equation holds true:

$$(\tan\psi)\lambda_1,\lambda_2 = \tag{39}$$

$$|\sigma_1 \cdot \sigma_2|\lambda_1,\lambda_2 \sqrt{\frac{(I_1)\lambda_1,\lambda_2}{(I_2)\lambda_1,\lambda_2 + (I_3)\lambda_1,\lambda_2 - (I_1)\lambda_1,\lambda_2}}$$

Therefore, ellipsometric parameters $\psi$ and $\Delta$ simultaneously obtained by substituting the values for the invariables, $\phi_{0\lambda_1}$, $\lambda_2$ and $|\sigma_1\sigma_2|\lambda_1$, $\lambda_2$. Values $\phi_{0\lambda_1}$ and $\phi_{0\lambda_2}$, both being invariables, can be corrected into cos $\Delta\lambda_1$ and cos $\Delta\lambda_2$.

Figure 8:
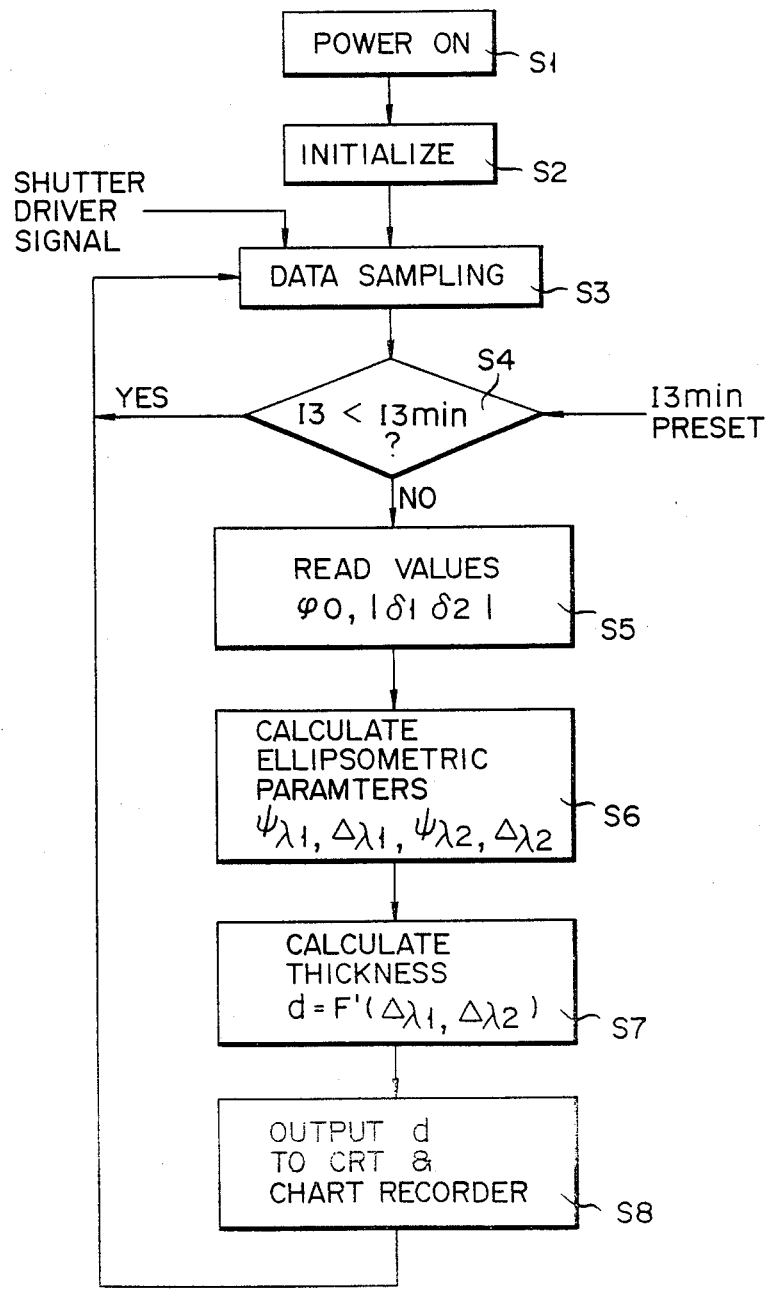
FIG. 8 is a flow chart explaining the operation of the microcomputer provided in the circuit shown in FIG. 7.

FIG. 8 is a flow chart explaining the operation of microcomputer 22 used in the third embodiment shown in FIGS. 6 and 7. The operation is identical to that of the microcomputer used in the first embodiment, except for the step of obtaining data about two different wavelengths $\lambda_1$ and $\lambda_2$. Therefore, it is not described in detail how microcomputer 22 functions in the third embodiment.

Let us assume that object 9 is a steel plate coated with an oil film. Amount M of oil coated on the steel plate is given:

$$M = \delta \times d \tag{40}$$

where $\delta$ is the density of the oil, and d is the thickness of the oil film. As is evident from equation (40), amount M and thickness d are proportionate to each other. When polarized beam having wavelength $\lambda_1$ of 633 nm, and a polarized beam having wavelength $\lambda_2$ of 514 nm are applied to object 9 at incidence angle $\phi_0$ of 70°, amount M can be given as follows, provided that coefficients A (82.8), B (−57.7) and C (1.61) in equation (29) have been obtained by experiment:

$$M = 82.8(\cos\Delta\lambda_2 - 0.697\cos\Delta\lambda_1 + 0.0294) \tag{41}$$

Hence, by substituting the actual values for cos $\Delta\lambda_1$ and cos $\Delta\lambda_2$, both contained in equation (41), we can obtain amount M of oil coated on the steel plate 9.

The present invention is not limited to the embodiment described above. It can be also applied to the case where the phase-cosines, cos $\Delta\lambda_1$ and cos $\Delta\lambda_2$, and the thickness d of the film have more general relationship with wavelengths $\lambda_1$ and $\lambda_2$:

$$\cos\Delta\lambda_1 = f_1(d) + \cos\Delta\lambda_{1,s} \tag{43}$$

$$\cos\Delta\lambda_2 = f_2(d) + \cos\Delta_{2,s} \tag{44}$$

where the following relation holds within a certain variation range of the substrate properties:

$$\cos\Delta\lambda_{2,s} = f_0(\cos\Delta\lambda_{1,s}) \tag{42}$$

where f0 is not necessary a linear function. Therefore:

$$\cos\Delta\lambda_2 - f_2(d) = f_0\{\cos\Delta\lambda_1 - f_1(d)\} \tag{45}$$

As has been described above, the apparatus of the third embodiment of the present invention are accurately measure the thickness of a thin film coated on an object even if the refractive index of the object and other physical properties thereof continuously change.

Figure 9:
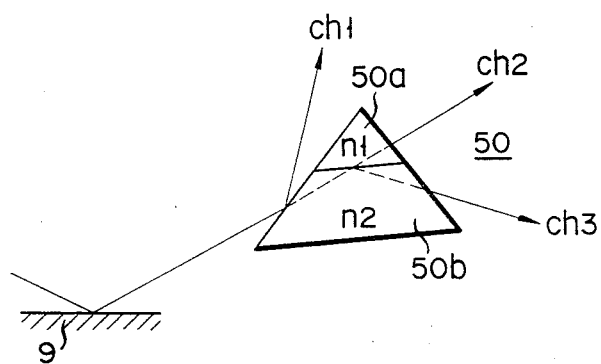
FIGS. 9 and 10 show modified optical systems to be used in the embodiments of the invention, respectively.
Figure 10:
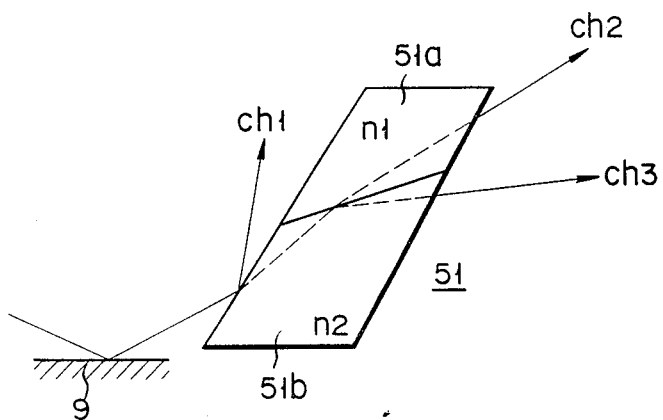

FIGS. 9 and 10 show other examples of the beam splitting means to be used for the four optical flats 13a–13d as in the first to third embodiments. FIG. 9 is a glass prism consisting of two portions 50a and 50b having refractive indices n1 and n2 (n1≠n2), respectively. As shown in FIG. 9, the incident light beam is splitted in the three beams ch1–ch3 by the glass prism 50. In the similar manner, the glass prism 51 of FIG. 10 having two portions 51a and 51b also can be used.

What is claimed is:

1. A film thickness-measuring apparatus comprising:
   circularly polarized light forming means for forming circularly polarized light which can be incident on an incidence plane of an object to be measured at a predetermined angle;
   beam splitter means for converting the light reflected by the object into a plurality of light beams;
   a plurality of analyzers for allowing the plurality of light beams obtained by said beam splitter means to pass at different transmission polarization azimuths, respectively;
   electrical signal output means for outputting electrical signals corresponding to light amounts/intensities of the plurality of light beams from said analyzers; and
   an arithmetic processing section for receiving the respective electrical signals from said electrical signal output means and performing predetermined arithmetic processing for the electrical signals to obtain an amplitude ratio and a phase of two ellipsometric parameters.

2. An apparatus according to claim 1, wherein said circularly polarized light forming means includes a monochromatic light source, a polarizer for converting output light from said light source into linearly polarized light, and a λ/4 plate for receiving the linearly polarized light and forming circularly polarized light.

3. An apparatus according to claim 2, wherein the amplitude ratio $\Delta$ and phase $\psi$ of the two ellipsometric parameters are calculated by said arithmetic processing section using the following equations, provided light intensity signals of the three light beams split by said three optical flats are I1, I2, and I3, respectively:

$$\sin(\Delta - \phi 0) = \{(I2 - I3)/2I1\} \sqrt{I1/(I2 + I3 - I1)}$$

$$\tan\psi = |\sigma 1 \sigma 2| \sqrt{I1/(I2 + I3 - I1)}$$

4. An apparatus according to claim 2, further comprising an optical modulator arranged between said light source and said polarizer, and means for synchronously detecting the electrical signals in synchronism with an operation of said optical modulator.

5. An apparatus according to claim 1, wherein said beam splitter means is arranged such that three optical flats of an identical material and shape are fixed parallel to each other, and split reflected light into three light beams.

6. An apparatus according to claim 1, wherein said signal output means comprises lens means for focusing the respective light beams transmitted through said analyzers at the same focal point, pinhole means located at the focal point, and photodetector means for forming electrical signals corresponding to intensities of the light beams transmitted through said pinhole means.

7. An apparatus according to claim 6, wherein film thickness d to be obtained is calculated as:

$$d = K\Delta$$

where K is a constant.

8. An apparatus according to claim 6, wherein when a focal length of said focusing lens means is f and a diameter of a pinhole of a pinhole plate is D, said apparatus has a measurement visual field set by:

$$D \leq 0.7 \times 10^{-3} f.$$

9. An apparatus according to claim 1, wherein said beam splitting means comprises four optical flats made of the same material, having the same shape, positioned parallel to each other, for splitting the light beam reflected from said film, into three light beams.

10. An apparatus according to claim 1, wherein said polarizer of said light-applying means applies at least two circularly polarized light beams having different wavelengths and a predetermined orientation angle, to a film at the same predetermined incidence angle in order to measure the thickness of the film.

* * * * *